United States Patent [19]
Martin

[11] Patent Number: 5,379,763
[45] Date of Patent: Jan. 10, 1995

[54] DISPENSING APPARATUS FOR POWDERED MEDICAMENTS

[75] Inventor: Trevor N. Martin, Norfolk, England

[73] Assignee: Bespak Plc, Norfolk, United Kingdom

[21] Appl. No.: 92,430

[22] Filed: Jul. 16, 1993

[30] Foreign Application Priority Data

Jul. 28, 1992 [GB] United Kingdom ............... 9216038

[51] Int. Cl.6 ............................................. A61M 15/00
[52] U.S. Cl. ............................ 128/203.15; 128/203.21; 128/203.23
[58] Field of Search ................... 128/203.15, 203.21, 128/203.12, 203.23

[56] References Cited

U.S. PATENT DOCUMENTS

| | | | |
|---|---|---|---|
| 3,653,380 | 4/1972 | Hansen | 128/203.15 |
| 4,098,273 | 7/1978 | Glenn | 128/203.15 |
| 4,147,166 | 4/1979 | Hansen | 128/203.15 |
| 4,227,522 | 10/1980 | Carris | 128/203.15 |
| 4,995,385 | 2/1991 | Valentini et al. | 128/203.21 |
| 5,048,514 | 9/1991 | Ramella | 128/203.21 |
| 5,152,284 | 10/1992 | Valentini et al. | 128/203.21 |

FOREIGN PATENT DOCUMENTS

| | | |
|---|---|---|
| 0406893A1 | 1/1991 | European Pat. Off. . |
| 2380032 | 9/1978 | France . |
| 2704574 | 8/1977 | Germany . |
| 2804852 | 8/1978 | Germany ............ 128/203.15 |
| 1504441 | 3/1978 | United Kingdom . |
| 1520062 | 8/1978 | United Kingdom . |
| 1520063 | 8/1978 | United Kingdom . |
| 1520064 | 9/1978 | United Kingdom . |
| 1561835 | 3/1980 | United Kingdom . |
| 1562732 | 3/1980 | United Kingdom . |
| 2061735 | 5/1981 | United Kingdom ........... 128/203.15 |
| 1591405 | 6/1981 | United Kingdom . |
| 2064334 | 6/1981 | United Kingdom . |
| 2064336 | 6/1981 | United Kingdom ........... 128/203.15 |
| 1598081 | 9/1981 | United Kingdom . |
| 2061735B | 11/1983 | United Kingdom . |

Primary Examiner—Edgar S. Burr
Assistant Examiner—Eric P. Raciti
Attorney, Agent, or Firm—Beveridge, DeGrandi, Weilacher & Young

[57] ABSTRACT

Capsules containing powder to be inhaled are received in a storage chamber within a tubular body of a dispensing apparatus. The chamber has a cylindrical portion along which capsules are fed to a dispensing station by a feed mechanism having feed members. An actuating sleeve overlays the body and is connected to the feed members which are moved into and out of the chamber by cam action. An end cap slidable on the body has a gripping means for gripping a forward portion of a capsule to enable the capsule to be opened at the dispensing station by pulling apart portions of the capsule. The apparatus allows capsules to be opened for inhalation of the contents and for the spent capsules to be ejected by movement of a single sleeve actuator relative to a body.

27 Claims, 8 Drawing Sheets

DISPENSING APPARATUS FOR POWDERED MEDICAMENTS

BACKGROUND OF THE INVENTION

This invention relates to dispensing apparatus for powdered medicaments supplied in capsules for inhalation therapy.

It is known to dispense powdered medicaments using apparatus in which capsules containing the powder are mechanically opened at a dispensing station where inhaled air subsequently entrains the powder which is then dispensed through a mouth piece.

GB1598081 discloses apparatus in which portions of a capsule are separated to release the powder, this technique being preferred to disrupting the capsule by piercing or crushing techniques which may result in debris from the capsule material being inhaled. A disadvantage of this apparatus is that individual capsules must be loaded prior to use and this may be a difficult procedure for some users.

GB2061735B discloses apparatus in which a feed mechanism in the form of a carousel delivers capsules to the dispensing station at successive actuations of an actuator which also operates a capsule opening means which separates portions of the capsule at the dispensing station ready for inhalation. The spent capsules are retained in the carousel and this has the disadvantage that it is possible for a spent capsule to be again presented at a subsequent actuation in the dispensing station when a complete revolution is completed. It is also difficult for the user to examine the spent capsule immediately following actuation in order to determine whether the powder has been entirely dispensed.

SUMMARY OF THE INVENTION

It is an object of the present invention to provide an improved feed mechanism and an apparatus which is simple for the user to operate.

It is a further objection of the present invention to provide an apparatus in which capsules are opened at a dispensing station by pulling apart forward and rearward portions of the capsule and subsequently ejecting the spent capsule portions.

It is a further object to achieve the operations of feeding, opening and ejecting the capsules by movement of a single actuator.

According to the present invention there is disclosed dispensing apparatus for use in the inhalation of medicaments supplied in capsules, the apparatus comprising a body having a capsule storage means receiving a number of capsules in use, an actuator movably mounted on the body, a feed mechanism operable at successive actuations of the actuator to feed successive capsules from the storage chamber to a dispensing station defining a dispensing chamber, capsule opening means operable in response to movement of the actuator to expose at the dispensing station the contents of the capsule within the dispensing chamber and a duct defining an airway communicating between the dispensing chamber and an outlet defined by the body through which air is inhaled in use, wherein the capsule storage means define a storage chamber having a cylindrical portion to receive capsules arranged in linear array and the feed mechanism comprises at least one feed member operable at successive actuations to move a capsule longitudinally along the cylindrical portion towards the dispensing station.

Preferably the actuator comprises a tubular sleeve overlaying the body and reciprocatingly movable relative to the body in a direction coaxial with the cylindrical portion.

Preferably the feed member is operatively connected to the actuator by a respective jaw facilitating movement of the feed member into and out of operative engagement with capsules within the cylindrical portion of the storage chamber.

The jaws may be formed integrally with the actuator such that the feed members are longitudinally movable in unison with the actuator and wherein the jaws are flexible to accommodate movement of the feed members relative to the actuator.

Alternatively the jaws may be formed separately from the actuator and the feed mechanism may further comprise biassing means operable between the body and the jaws to bias the jaws longitudinally towards the dispensing station, the actuator being engagable with the jaws to move the jaws away from the dispensing station and operable to release the jaws for travel towards the dispensing station by action of the biassing means.

Preferably the body is provided with first cam formations cooperable with the feed members such that the jaws are moved to a closed position during at least part of forward longitudinal motion of the jaws towards the dispensing station and are retracted to an open position during return motion of the jaws relative to the body, the closed position of the jaws corresponding to the respective feed member being operatively engageable with a capsule within the cylindrical portion and the open position corresponding to the feed member being retracted out of operative engagement with the capsules.

Preferably the apparatus further comprises a generally tubular end cap into which the body extends longitudinally, the end cap comprising a first gripping means operable to grip a forward portion of a capsule at the dispensing station, the body comprising second gripping means operable to grip a rear portion of a capsule at the dispensing station, the end cap being movable relative to the body in response to movement of the actuator whereby the first and second gripping means are relatively movable to effect separation of the first and second portions and thereby constitute the capsule opening means.

Conveniently the apparatus comprises latch means operable between the body and the end cap to retain the end cap in a fixed position relative to the body during a first stage of movement of the actuator relative to the body and to release the end cap from the body so as to travel in unison with the actuator during a second stage of motion of the actuator relative to the body.

The latch means conveniently comprises at least one latch member connected to the end cap and cooperable with a respective recess formed in the body to prevent relative motion between the end cap and the body and wherein the actuator comprises second cam formations cooperable with respective latch members to control the operation thereof according to the position of the actuator relative to the body.

In a preferred embodiment the end cap defines a passageway receiving the forward portion of a capsule and the first gripping means comprises an O-ring located in the passageway.

Preferably the passageway communicates with an ejection aperture defined by the end cap and through which spent capsules are ejected in use.

Spent capsules may thereby be inspected by the user after use in order to confirm that the powder has been fully dispensed.

Conveniently the second gripping means comprises a collet of variable diameter and defining an aperture through which a capsule is received at the dispensing station, the end cap being provided with third cam formations cooperable with the collet to reduce the aperture in response to movement of the end cap relative to the body to thereby grip the rear portion of a capsule.

Preferably the apparatus comprises means for creating turbulence in the air flow in the dispensing chamber during inhalation.

Conveniently the body comprises a mouthpiece defining the outlet, the mouthpiece being connected to a tube defining the storage chamber, the mouthpiece and the tube being removably connected to a main portion of the body to provide access to the storage chamber.

According to a further aspect of the present invention there is disclosed a method of dispensing for inhalation medicaments supplied in capsules comprising the steps of locating a number of capsules in a capsule storage means defined by a body, operating a feed mechanism by movement of an actuator relative to the body to feed a capsule from the storage means to a dispensing station, operating a capsule opening means at the dispensing station by movement of the actuator relative to the body to expose the contents of the capsule within a dispensing chamber and inhaling a flow of air through an outlet communicating with the dispensing chamber via an airway such that the contents of the capsules are entrained in the flow of inhaled air, wherein the method comprises locating the capsules in linear array in a cylindrical portion of a storage chamber defined by the capsule storage means and wherein the feed mechanism is operable at successive actuations to move a capsule longitudinally along the cylindrical portion towards the dispensing station by action of at least one feed member of the feed mechanism.

Conveniently the method includes the step of ejecting a portion of a spent capsule by action of the feed mechanism feeding a next successive capsule into the dispensing station to thereby displace the spent capsule portion.

Specific embodiments of the present invention will now be described by way of example only and with reference to the accompanying drawings of which.

Figures 1, 2, 3, 4, 5:
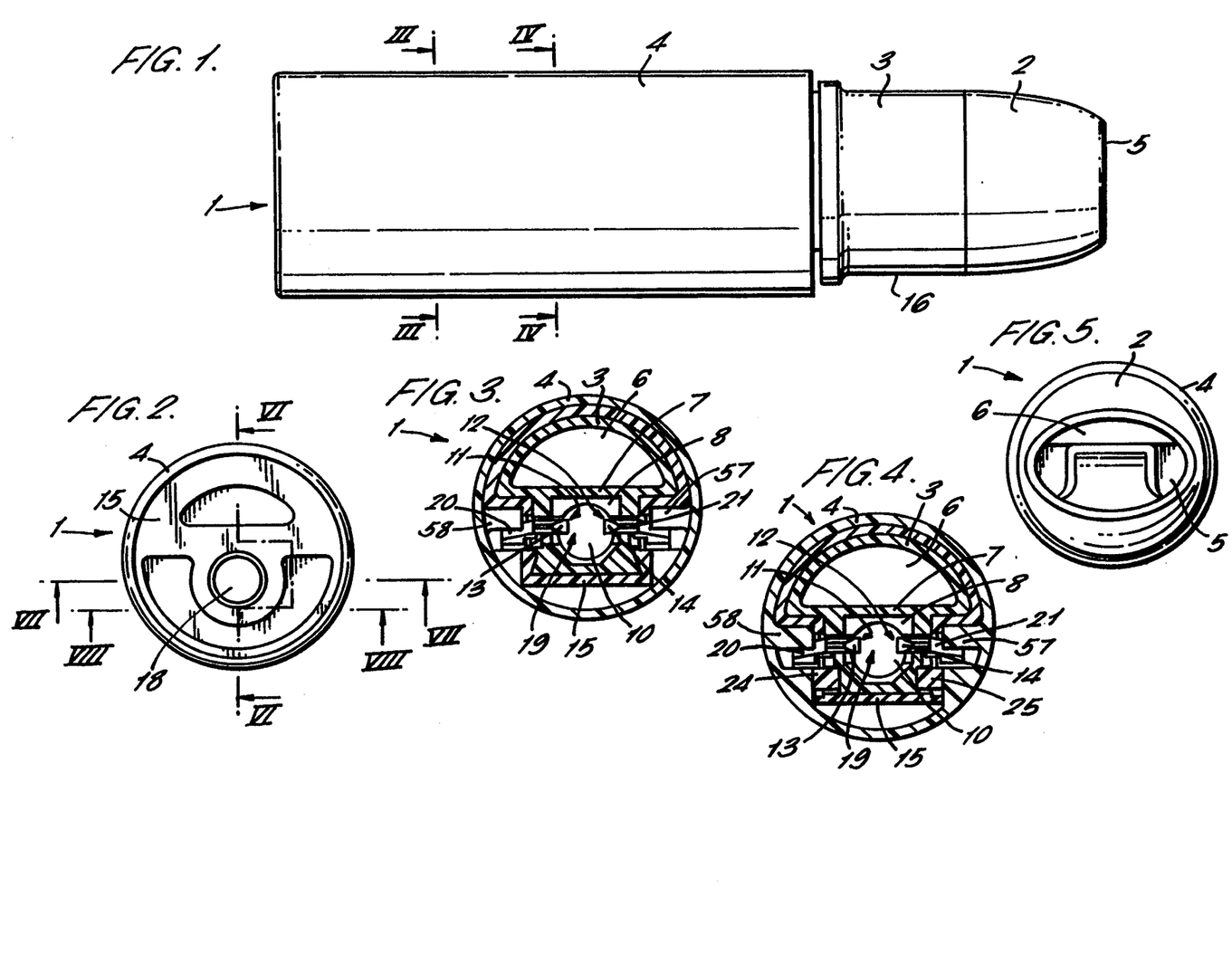
FIG. 1 is a side elevation of dispensing apparatus in accordance with the present invention in the rest position.
FIG. 2 is an end elevation of the apparatus of FIG. 1 viewed from left to right.
FIG. 3 is a transverse section of the apparatus of FIG. 1 taken at III—III during the first stage of movement.
FIG. 4 is a transverse section of the apparatus of FIG. 1 taken at IV—IV during the first stage of movement.
FIG. 5 is an end view of the apparatus of FIG. 1 viewed from right to left.

In FIG. 1 an apparatus 1 comprises a mouthpiece 2 connected to a body 3 which projects from a generally tubular sleeve 4.

As shown in the end view of FIG. 5 the mouthpiece 2 defines an orifice 5 communicating with an airway 6 which extends longitudinally of the apparatus 1 and is also visible in the transverse section views of FIGS. 3 and 4.

The body 3 is generally tubular but of part-circular and part rectangular profile as is evident from FIGS. 3 and 4, the body having a planar partition 7 which separates the airway 6 of part circular profile from a conduit 8 extending longitudinally of the apparatus.

Figure 7:
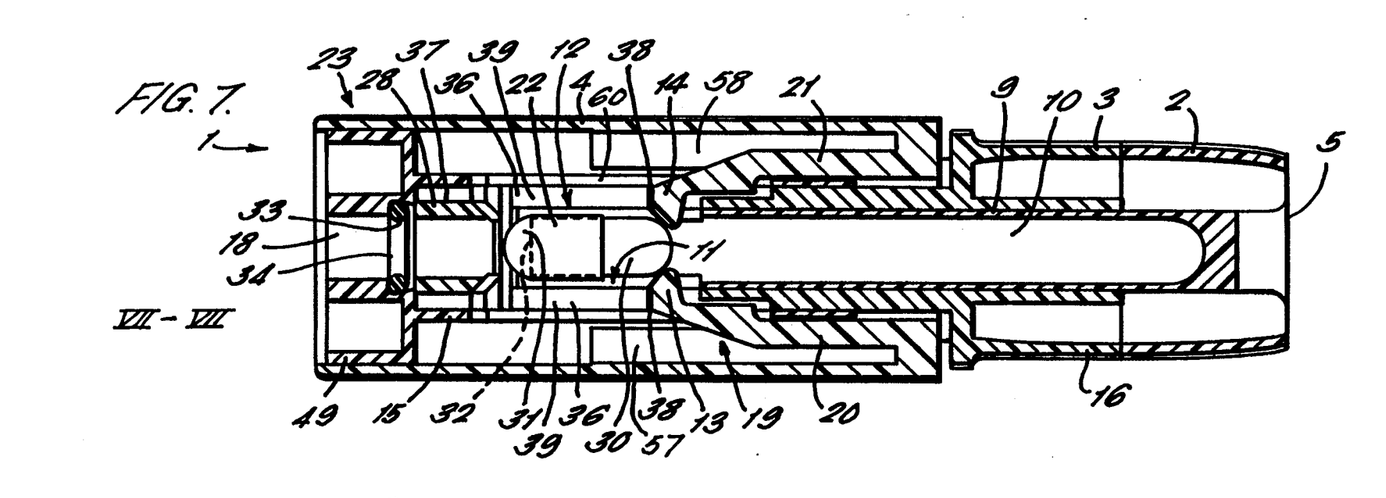
FIG. 7 is a horizontal section taken at VII—VII with reference to FIG. 2 of the apparatus of FIG. 1 in its rest position.

As shown in FIG. 7 the mouthpiece 2 is formed integrally with a tube 9 defining a capsule storage chamber 10, the tube 9 being accommodated within the conduit 8 such that the capsule storage chamber extends longitudinally of the apparatus 1.

The tube 9 is provided with left and right-hand slots 12 and 11 respectively which extend longitudinally of the tube 9. The slots 12 and 11 allow left and right-hand feed members 14 and 13 respectively to project into the capsule storage chamber 10 and to be capable of longitudinal motion as part of a feed mechanism for moving capsules linearly along the chamber 10.

The body 3 is inserted within a tubular end cap 15 which in turn is received as a sliding fit within the sleeve 4. The body 3 therefore has a mouthpiece end portion 16 which is connected to the mouthpiece 2 and a distal end portion 17 which is received within and which is closed by the end cap 15. The end cap 15 is provided with a cylindrically shaped capsule ejection aperture 18 which is coaxially in alignment with the capsule storage chamber 10. The end cap 15 is also provided with slots 60 as seen in FIG. 7 allowing the jaws 21 and 20 to project from the sleeve 4 into the slots 12 and 11.

During a complete cycle of operation of the apparatus 1 the sleeve 4 moves relative to the body 3 in four distinct successive stages of motion. During a first stage the sleeve 4 moves away from the mouthpiece 2 while the end cap 15 remains static relative to the body 3. During the second stage the sleeve continues to move away from the mouthpiece 2 but the end cap 15 moves in unison with the sleeve 4. During the third stage the sleeve 4 and the end cap 15 move in unison towards the mouthpiece 2. During the fourth stage the end cap 15 is retained in its static position relative to the body 3 and the sleeve 4 continues to move towards the mouthpiece 2.

Actuation for this movement is provided by the user gripping with one hand the mouthpiece end portion 16 of the body 3 and with the other hand the sleeve 4 and then moving the sleeve 4 relative to the body.

During the first stage of movement the motion of the sleeve 4 actuates a capsule feed mechanism 19 as shown in FIG. 7, the feed mechanism comprising the feed members 14 and 13 which are connected to the sleeve 4 by respective left and right feed jaws 21 and 20. As seen in FIG. 7 the feed members 13 and 14 are arranged to push a capsule 22 in a direction away from the mouthpiece 2 and towards a dispensing station 23.

During this first stage of movement the end cap 15 is prevented from moving relative to the body 3 by left and right-hand latch members 25 and 24 respectively which are formed integrally with the end cap and which are cooperable with left and right-hand latch recesses 27 and 26 respectively formed as indentations in the body 3.

Figure 8:
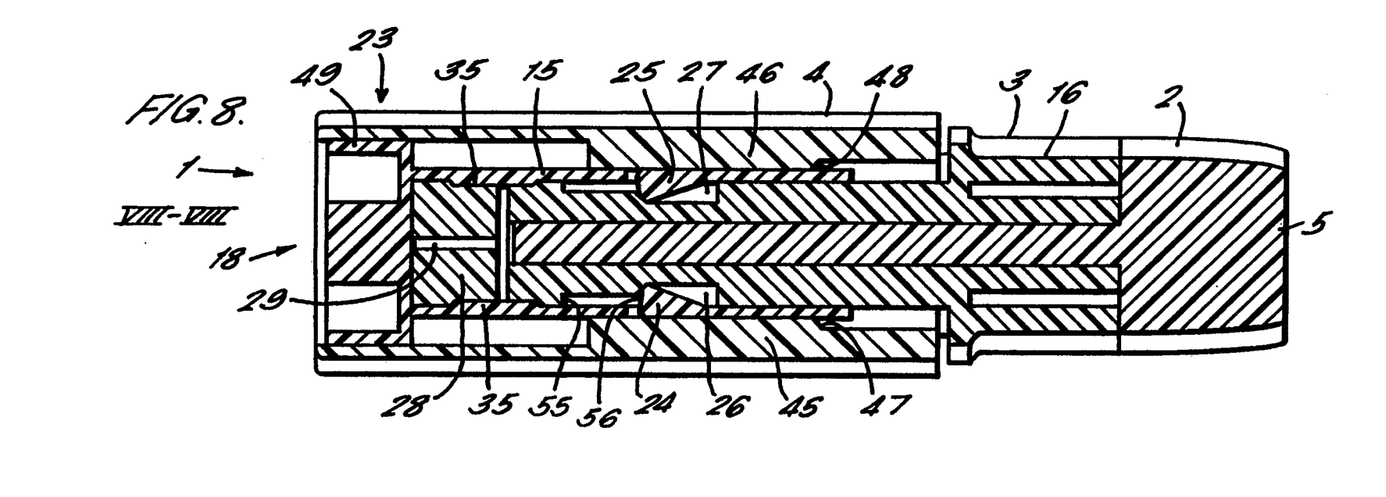
FIG. 8 is a horizontal section taken at VIII—VIII of the apparatus of FIG. 1 in its rest position.

The distal end portion 17 of the body 3 is provided with a collet 28 which is split by a radially extending slot 29 as shown in FIG. 8 so as to allow the diameter of the collet to be varied in order to grip the capsule 22. Each capsule 22 is inserted in the storage chamber 10 in a specific orientation in which a capsule body 30 is directed so as to be facing the mouthpiece 2 and a capsule cap 31 is directed so as to be facing away from the mouthpiece, the capsule body being of smaller diameter than the cap such that an open mouth 32 of the capsule body is received within and closed by the cap 31.

Figure 9:
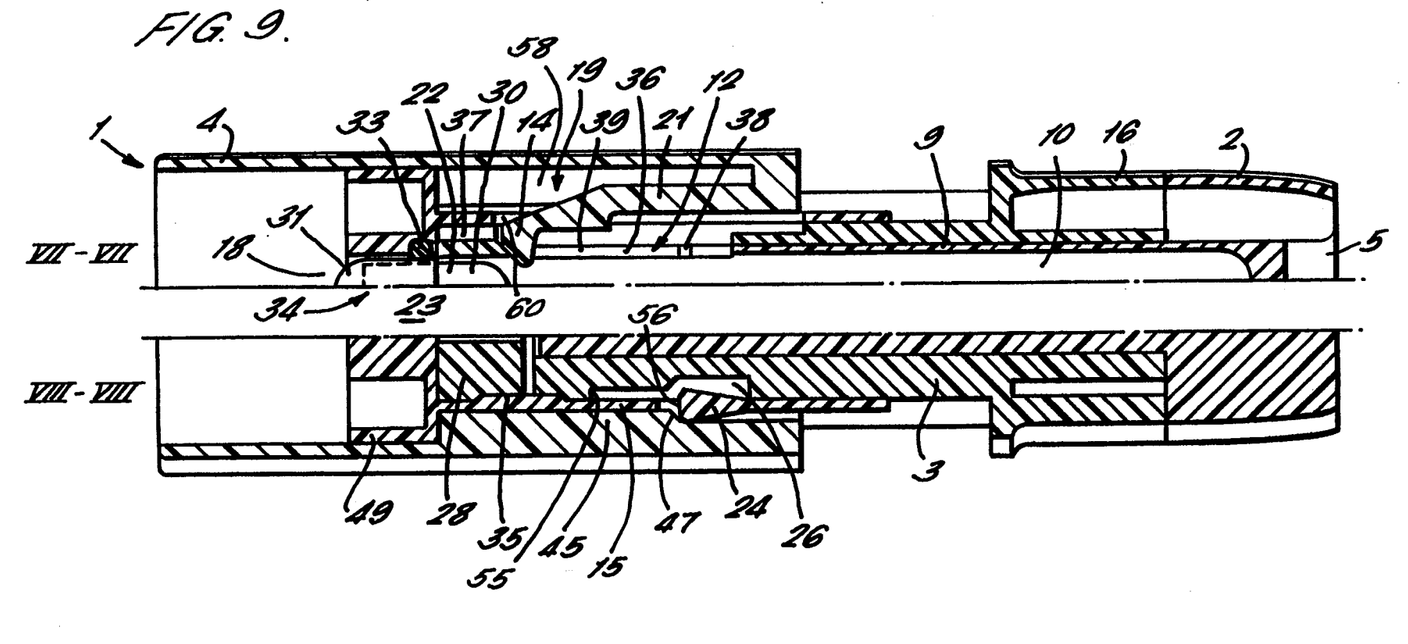
FIG. 9 is a two-part horizontal section of the apparatus at the commencement of its second stage of actuation, the upper portion being viewed at VII—VII and the lower portion being viewed at VIII—VIII.

During the first stage of movement a capsule 22 is pushed towards the dispensing station 23 so as to extend through the collet 28 as illustrated in FIG. 9 in which the capsule body remains within the collet and the capsule cap projects beyond the collet into the capsule ejection aperture 18.

Figure 11:
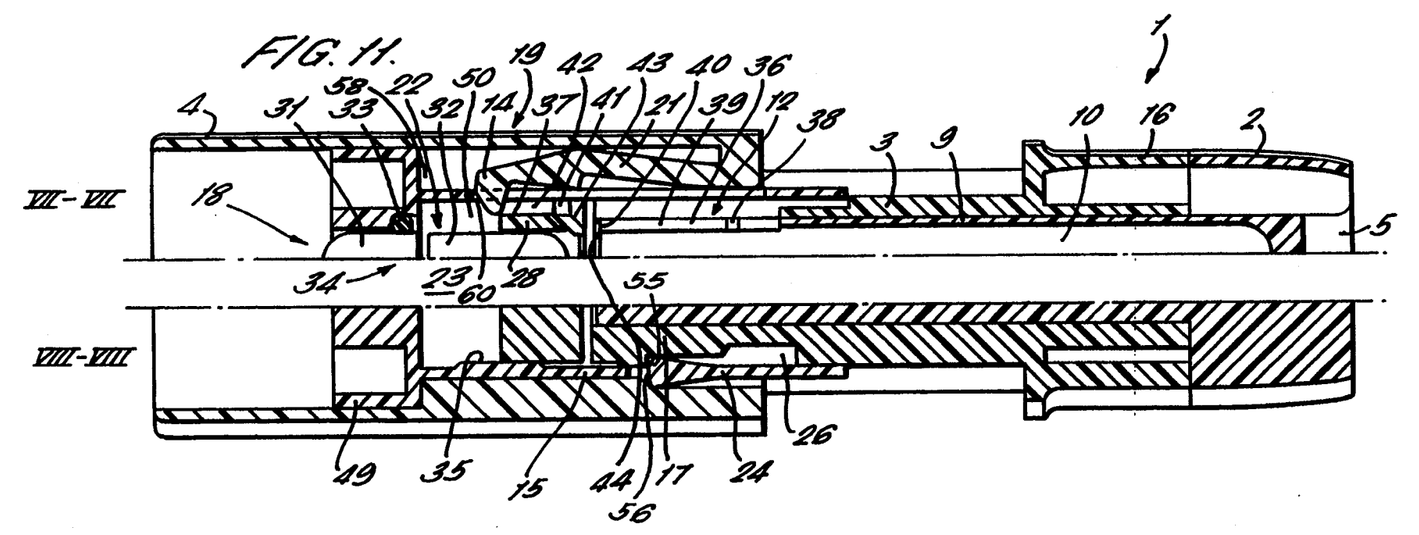
FIG. 11 is a two-part horizontal section of the apparatus at the end of the second stage of actuation in which the upper portion of the Figure is viewed at VII—VII and the lower portion is viewed at VIII—VIII.

An O-ring 33 located in the entrance 34 of aperture 18 is dimensioned so as to be a sliding fit over the capsule cap 31 and to provide a degree of frictional resistance to such sliding motion. As shown in FIG. 11 the O-ring 33 grips the capsule cap 31 such that, with the capsule body 30 being gripped by the collet 28, relative movement between the body 3 and the end cap 15 during the second stage of movement results in separation of the capsule body and cap.

The collet 28 is radially compressed during the second stage of movement so as to have a reduced diameter which grips the capsule body 32, the radial compression being the result of cam action provided by a radially inward projection 35 formed on the end cap 15 as shown in the lower half of FIG. 11. Compression of the collet continues throughout the third stage of movement and is released at the end of the third stage of movement at which time the end cap 15 has returned to its rest position relative to the body 3.

Motion of the feed members 13 and 14 in providing feeding of capsules relies upon the action of a first cam track 36 formed on the body 3 and a second cam track 37 formed on the collet 28 which is also an integral part of the body 3. In the rest position of FIG. 6 the jaws 20 and 21 lie in a horizontal plane with the jaws in a closed position in which feed members 13 and 14 are in close proximity with one another and extend into the chamber 10. At the commencement of the first stage of movement the sleeve 4 begins to move relative to the body 3 and the feed members 13 and 14 move with the sleeve and encounter upwardly sloping ramps 38 provided by the first cam track 36.

Figure 6:
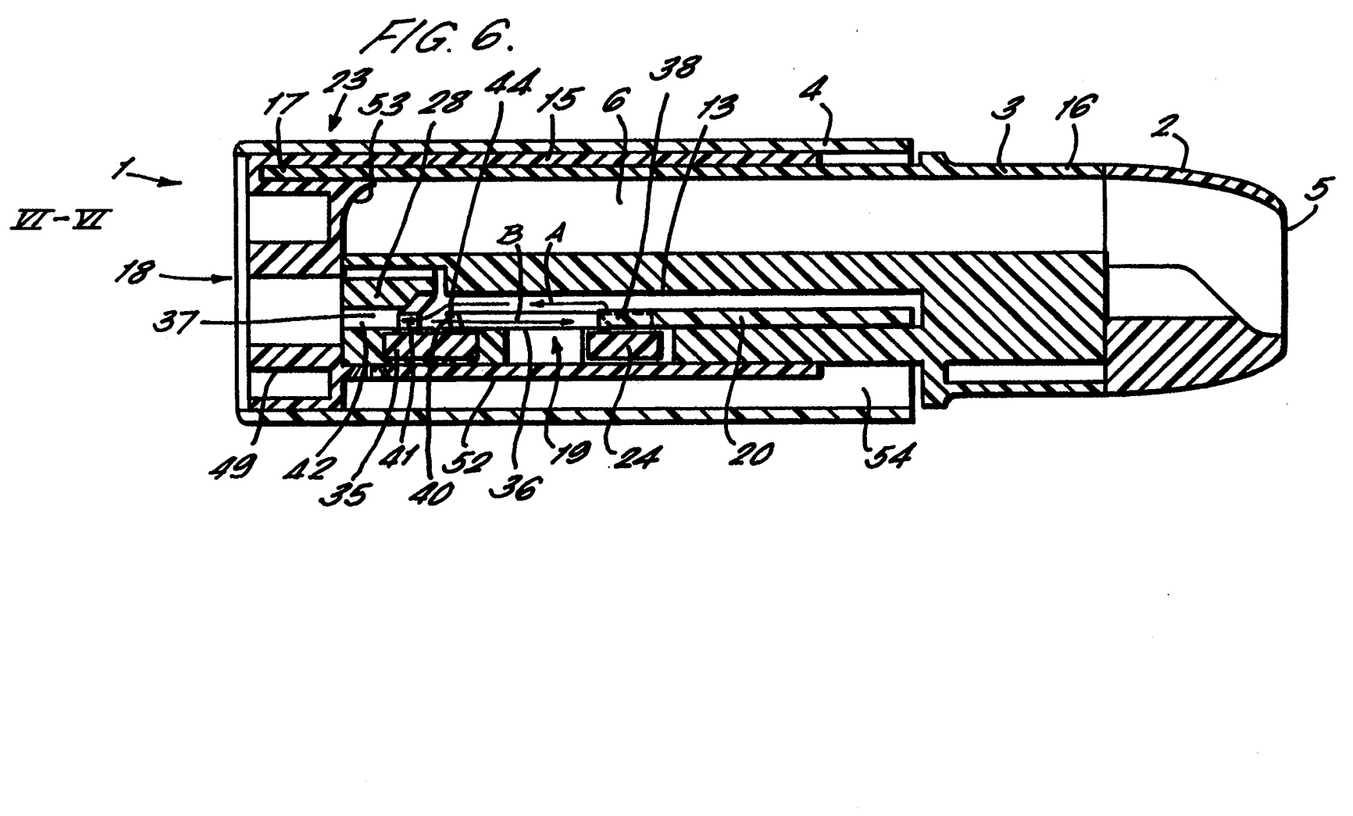
FIG. 6 is a staggered longitudinal section through the apparatus of FIG. 1 in the rest position taken at VI—VI with reference to FIG. 2.

The jaws 20 and 21 are bent such that the feed members 13 and 14 are raised above the initial horizontal plane of the jaws and continued motion during the first stage of movement results in the feed members 13 and 14 riding along horizontal upper surfaces 39 of the first cam track 36 as shown by arrow A in FIG. 6. The raised positions of the feed members 13 and 14 can also be seen in FIGS. 3 and 4. In this raised position the jaws 20, 21 are prevented from opening by the presence of stops 57 and 58 projecting inwardly of the sleeve 4 as seen in FIGS. 3 and 4. In the rest positions of the jaws 20, 21 the jaws assume the closed position shown in FIG. 7 by virtue of shape memory.

At the end of the first stage of movement the feed members 13 and 14 encounter a downward step 40 provided by the first cam track 36 and the jaws 20 and 21 return to their original horizontal planar position.

Throughout the first stage of movement a capsule 22 is moved forwardly by the feed members 13 and 14 towards the dispensing station 23.

At the beginning of the second stage of movement the feed members 13 and 14 encounter upwardly sloping ramps 41 formed externally on the collet 28 and the jaws are upwardly deflected allowing the feed members 13 and 14 to travel along a horizontal upper surface 42. The upwardly sloping ramps 41 are complemented by laterally deflecting ramps 43 arranged to move the jaws into an opened position in which the feed members 13 and 14 are moved clear of the capsule 22 and are external of the chamber 10 as shown in FIG. 11.

During the third stage of movement the feed members 13 and 14 return along the horizontal upper surfaces 42 and descend the ramps 41. At the start of the fourth stage of motion the feed members 13 and 14 encounter laterally deflecting ramps 44 which deflect the feed members so as to open the jaws 20 and 21 whilst retaining the jaws in their original horizontal plane. During the fourth stage of motion the feed members 13 and 14 are returned to their original rest position as shown in FIG. 6 whilst the jaws are held open and the feed members are clear of the storage chamber 10. At the end of the fourth stage of motion the feed members 13 and 14 reach the end of the first cam track 36 and snap back to their rest position in which the jaws 20 and 21 are closed.

Return motion of the feed members during the fourth stage of motion is shown by arrow B in FIG. 6.

During the first stage of motion the sleeve 4 prevents the latch members 24 and 25 from moving out of engagement with the recesses 26 and 27 in the body 3 by contact between left and right latch retaining shoulders 46 and 45 respectively. The shoulders 45 and 46 terminate in ramped surfaces 47 and 48 respectively which are encountered by the latch members 24 and 25 at the commencement of the second stage of motion. The latch members 24 and 25 are then able to move transversely outwardly relative to the body 3 and out of the recesses 26 and 27. The end cap 15 is then unlatched from the body 3 throughout the second and third stages of motion and moves in unison with the sleeve 4. During the second stage of motion the longitudinal motion of the end cap 15 relative to the body is sufficient to open the capsule 22 so as to leave a gap of 1 mm between the capsule body 30 and the capsule cap 31. At the end of the second stage of motion the travel of the end cap 15 is limited by contact between forward ends 56 of the latch members 45, 46 and shoulders 55 provided by the latch recesses 26, 27.

Figure 10:
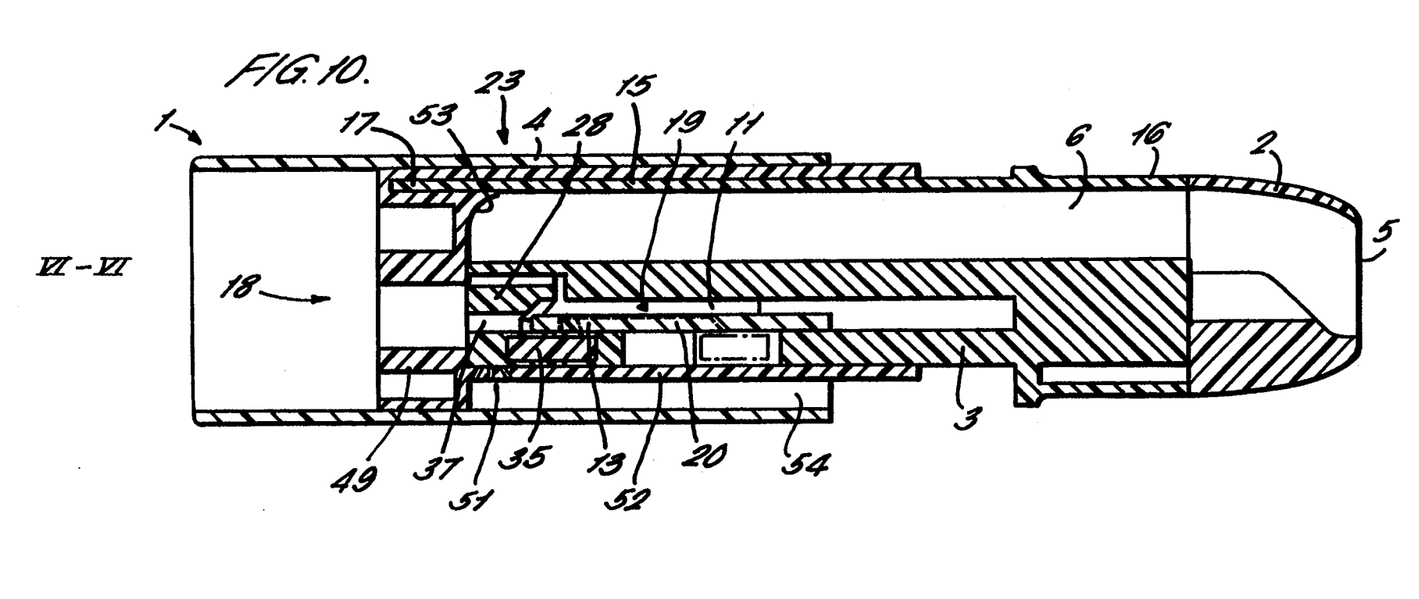
FIG. 10 is a staggered vertical elevation taken at VI—VI of the apparatus at the commencement of the second stage of actuation.
Figure 12:
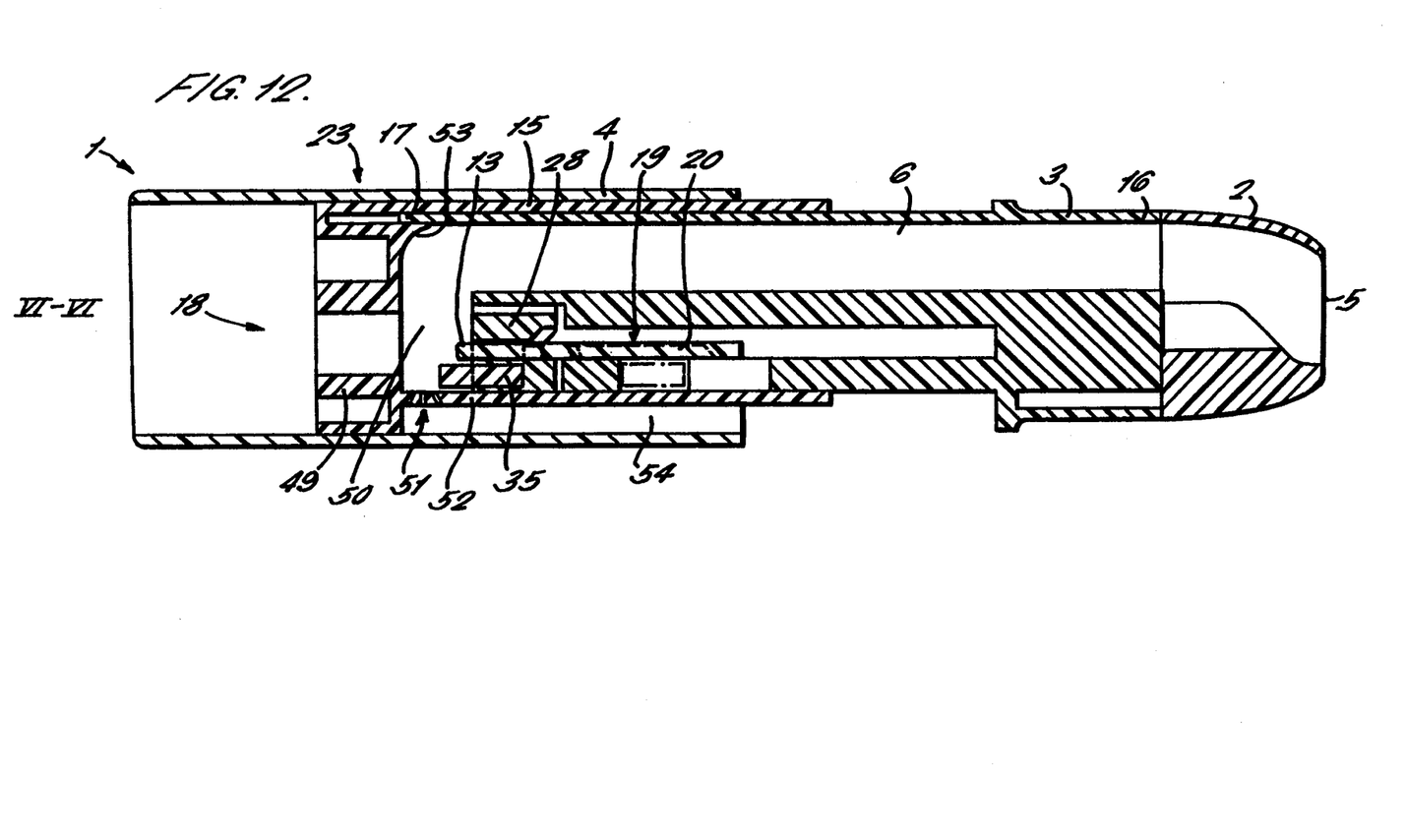
FIG. 12 is a longitudinal section taken at VI—VI at the end of the second stage of actuation.

The dispensing station 23 comprises an end portion 49 of the end cap 15 and the collet 28 which co-operate to separate the capsule 22 as described above. When moving apart during the second stage of motion a dispensing chamber 50 is created as shown in FIGS. 11 and 12 through which air is drawn by the user who inhales at the mouthpiece orifice 5 so as to draw air through the airway 6. The airway 6 communicates with the dispensing chamber 50 and air is drawn into the dispensing chamber 50 through inlet slots 51 which are provided in a side wall 52 of the end cap 15 as shown in FIGS. 6, 10 and 12. The end portion 49 of the end cap 15 has a smoothly curved surface 53 arranged at the upper end of the dispensing chamber 50 so as to smoothly deflect air from an upward vertical direction to longitudinal flow through the airway 6.

Air is supplied to the inlet slots 51 through an intake channel 54 provided between the sleeve 4 and the side wall 52 of the end cap 15.

The slots 51 comprise three individual slots which are angled with respect to one another so as to create turbulence within the dispensing chamber 50 in the vicinity of the mouth 32 of the capsule body 30 when opened.

In use, the capsule storage chamber 10 is filled with capsules arranged in linear array, the capsules being oriented such that the body 30 of each capsule 22 is closer to the mouthpiece 2 than the cap 31. The tube 9 of the mouthpiece 2 is inserted into the end cap 15 such that the leading capsule shown as 22 in FIG. 7 is forward of the feed members 13 and 14. In order for the leading capsule 22 to pass beyond the feed members 13 and 14 it is necessary for the jaws 20, 21 to open sufficiently for the capsule to pass. This is accommodated by pushing the tube 9 so as to urge the capsule between the feed members 13 and 14.

The user holds the mouthpiece 2 in one hand and the sleeve 3 in the other hand and pushes the sleeve away from the mouthpiece during a first stage of motion. The feed members 13 and 14 are moved upwardly by action of the ramps 38 to a position where they engage the capsule 22 and further motion of the sleeve results in capsule 22 being pushed forwardly in a direction away from the mouthpiece 2 towards the dispensing station 23. The cap 31 of the capsule 22 is pushed through the O-ring 33 whilst the body 30 remains located within the collet 28 in which it is retained as a loose fit as shown in FIG. 9.

The second stage motion then begins in which the collet 28 is reduced in diameter by action of projection 35 thereby closing around the body 30 and gripping the body firmly against axial motion within the chamber 10. At the same time the feed members 13 and 14 are withdrawn from the chamber 10 as the jaws 20, 21 open as a result of cam action with the second cam track 37.

At the same time the latch members 24 and 25 are released from the recesses 26 and 27 and during the second stage of motion the sleeve moves in unison with the end cap 15 away from the mouthpiece 2. During this motion the capsule 22 is opened by movement of the cap 31 away from the body 30 until the exposed mouth 32 of the capsule body is spaced from the cap by a distance of 1 mm.

At the end of the second stage of motion the dispensing chamber 50 is formed by separation of the end cap 15 from the body 3 and the apparatus 1 is ready for inhalation to take place.

The user inhales through the mouthpiece thereby drawing air through the dispensing chamber 50 and powder from within the capsule 22 is entrained in the air flow and inhaled.

Turbulence within the dispensing chamber 50 is created by the slots 51 thereby ensuring that the full dose is entrained in the air flow.

The third stage of motion is then commenced in which the sleeve returns in a direction towards the mouthpiece 2 to the position shown in FIG. 9, the end cap 15 moving in unison during this stage of motion and the feed members 13 and 14 returning to engage the laterally deflecting ramp 44. The user then turns the apparatus 1 into an orientation in which the mouthpiece 2 is uppermost so that capsules within the storage chamber 10 move under gravity towards the dispensing station. A new capsule then occupies the part of the dispensing chamber 10 which coincides in longitudinal extent with the first cam track 36.

Continued motion into the fourth stage of motion then follows in which the feed members 13 and 14 return to their rest positions adjacent the ramps 38 so as to close behind the new capsule and retain it in position.

During the third stage of the motion the cap 31 of capsule 22 will typically not become re-assembled with the capsule body 30 and will interfere with the open mouth 32 of the body such that the cap 31 will be ejected from the apparatus leaving the capsule body 30 in situ.

During the next successive dispensing operation the first stage of motion will advance a capsule forward to the dispensing station thereby displacing from the capsule ejection aperture the spent capsule body 30 from the preceding actuation.

Figure 13:
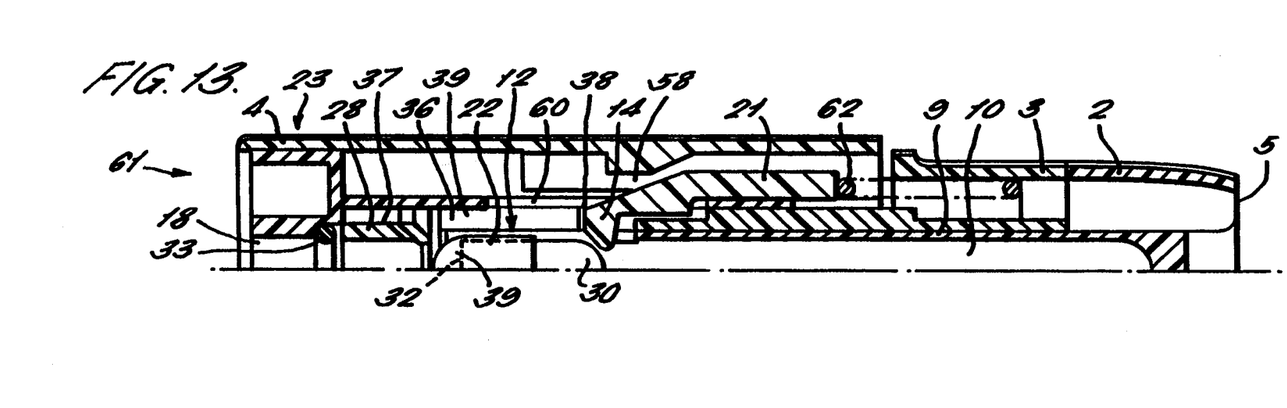
FIG. 13 is a view corresponding to that of FIG. 7 of a modified apparatus.
Figure 14:
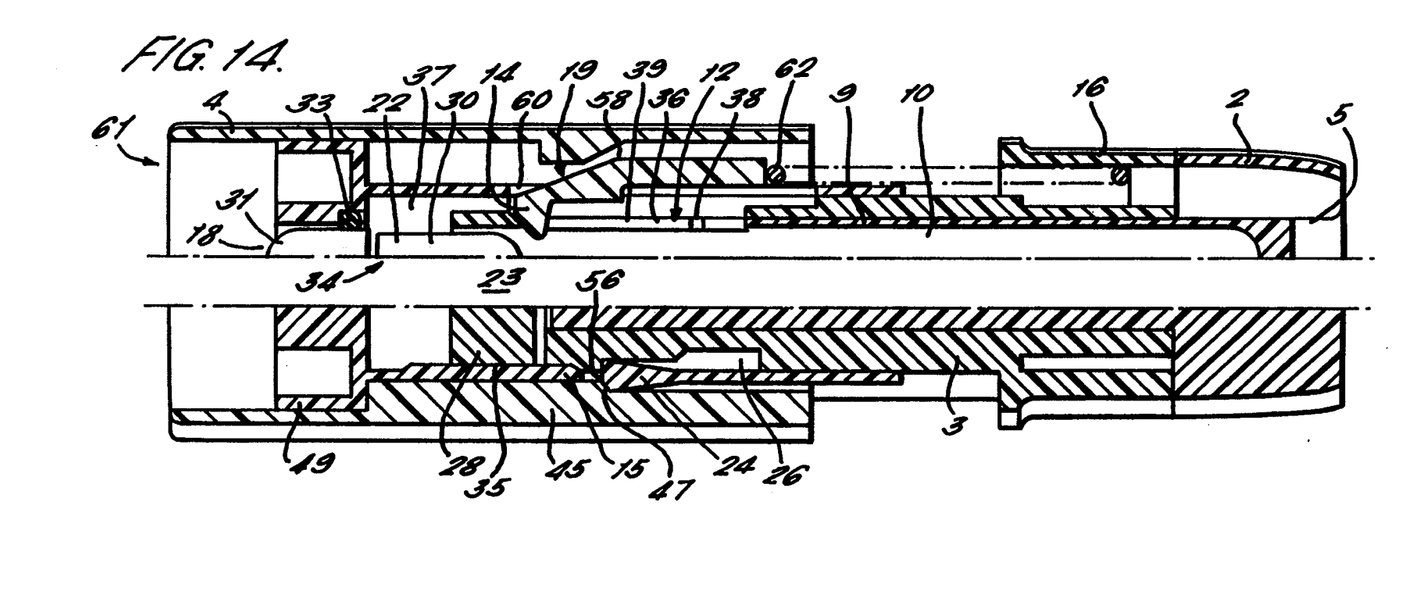
FIG. 14 is a view corresponding to FIG. 9 of the modified apparatus of FIG. 13.

A modified apparatus 61 is shown in FIGS. 13 and 14 and will be described using corresponding reference numerals to those of preceding Figures where appropriate for corresponding elements.

The modified apparatus 61 differs primarily from the apparatus 1 in that jaw members 20 and 21 together with feed members 13 and 14 are formed separately from the sleeve 4. The jaws 20 and 21 are biassed towards the dispensing station 23 by a compression spring 62 mounted on the body 3 and extending into the mouth piece 2.

The sleeve 4 is provided with a catch mechanism (not shown) which is operable to control the longitudinal movement of the jaws 20 and 21 such that during the fourth stage of movement the jaws are returned to their rest position as shown in FIG. 13 in which they are furthermost from the dispensing station 23 and whereby upon reaching the end of travel during the fourth stage of movement the jaws are released so as to travel under influence of the spring 62 in a direction towards the dispensing station.

This movement automatically feeds the next capsule 22 forward into the dispensing station and at the same time ejects the spent capsule body 30 of the preceding actuation.

The end cap 15 of the modified apparatus 61 has slots 60 which do not extend into the dispensing station 23 in the manner of the slots 60 of apparatus 1. Forward travel of the feed members 13 and 14 of the modified apparatus 61 is limited to a position shown in FIG. 14, this limit of travel being accommodated since the jaws 20 and 21 are not formed integrally with the sleeve 4.

One advantage of the modified apparatus 61 is that ejection of the spent capsule is completed at the end of the fourth stage of operation. The spent capsule may therefore be inspected immediately following an inhalation by a user to ensure that the contents of the capsule have been fully dispensed.

A further advantage is that, because the slots 60 do not extend into the dispensing station 23, the inlet of air to the dispensing chamber 50 is limited to the intake channels 54 thereby allowing the intake of air to be more precisely controlled.

In a further alternative arrangement (not shown) the capsule storage chamber 10 may be connected to a bulk reservoir of capsules from which capsules are fed into the capsule storage chamber where they form in linear array ready for feeding by the feed mechanism defined by the jaws 20 and 21, the feed members 13 and 14 and the first and second cam tracks 36 and 37.

In an alternative arrangement the storage chamber 10 may be provided by a disposable tube which is pre-packed with a supply of capsules.

Alternative gripping mechanisms may be employed for separating the two parts of the capsules. Such mechanisms may be adapted if required to accommodate any orientation of the capsule so that for example the capsules could be fed to the dispensing station with the capsule body being forward.

Alternative mechanisms may be provided for ejecting spent capsules and in particular the spent capsule may be ejected at the end of the second stage of motion in order to provide confirmation that the contents of the capsule have been fully dispensed.

For ease of manufacture, the slots 51 may be reconfigured so as to extend longitudinally instead of transversely relative to the end cap. Such an arrangement is easier to mould using axially moving mould parts.

I claim:

1. Dispensing apparatus for use in the inhalation of medicaments supplied in capsules, the apparatus comprising a body having a capsule storage means receiving a number of capsules in use, an actuator movably mounted on the body, a dispensing station defining a dispensing chamber, a feed mechanism operable at successive actuations of the actuator to feed successive capsules from the storage chamber to the dispensing station, capsule opening means operable in response to movement of the actuator to expose at the dispensing station the contents of the capsule within the dispensing chamber and a duct defining an airway communicating between the dispensing chamber and an outlet defined by the body through which air is inhaled in use, wherein the capsule storage means defines a storage chamber having a cylindrical portion to receive capsules arranged in linear array, said cylindrical portion oriented toward said dispensing station, and the feed mechanism comprises at least a first feed member means operable at successive actuations for pushing a capsule longitudinally along the cylindrical portion towards the dispensing station.

2. Apparatus as claimed in claim 1 wherein the actuator comprises a tubular sleeve overlaying the body and reciprocatingly movable relative to the body in a direction coaxial with the cylindrical portion.

3. Apparatus as claimed in claim 1 comprising means for creating turbulence in the air flow in the dispensing chamber during inhalation.

4. Apparatus as claimed in claim 1 wherein the body comprises a mouthpiece defining the outlet, the mouthpiece being connected to a tube defining the storage chamber, the mouthpiece and the tube being removably connected to a main portion of the body to provide access to the storage chamber.

5. Apparatus as claimed in claim 1 wherein the first feed member means is operatively connected to the actuator by a jaw facilitating movement of the first feed member means into and out of operative engagement with capsules within the cylindrical portion of the storage chamber.

6. Apparatus as claimed in claim 5 wherein the jaw is formed integrally with the actuator such that the first feed member means is longitudinally movable in unison with the actuator and wherein the jaw is flexible to accommodate movement of the first feed member relative to the actuator.

7. Apparatus as claimed in claim 5 wherein the jaw is formed separately from the actuator and wherein the feed mechanism further comprises biassing means operable between the body and the jaw to bias the jaw longitudinally towards the dispensing station, the actuator being engageable with the jaw to move the jaw away from the dispensing station and operable to release the jaw for travel towards the dispensing station by action of the biassing means.

8. Apparatus as claimed in claim 5 wherein the feed mechanism further comprises a second feed member means operable at successive actuations for pushing a capsule longitudinally along the cylindrical portion towards the dispensing station, the first and second feed member means being connected to the actuator by respective jaws facilitating movement of the first and second feed member means into and out of operative engagement with capsules within the cylindrical portion of the storage chamber, and wherein the body is provided with first cam formations cooperable with the first and second feed member means such that the jaws are moved to a closed position during at least part of forward longitudinal motion of the jaws towards the dispensing station and are retracted to an open position during return motion of the jaws relative to the body, the closed position of the jaws corresponding to the feed member means being operatively engageable with a capsule within the cylindrical portion and the open position corresponding to the feed member means being retracted out of operative engagement with the capsules.

9. Apparatus as claimed in claim 1 further comprising a generally tubular end cap into which the body extends longitudinally, the end cap comprising a first gripping means for gripping a forward portion of a capsule at the dispensing station, the body comprising second gripping means for gripping a rear portion of a capsule at the dispensing station, the end cap being movable relative to the body in response to movement of the actuator whereby the first and second gripping means are relatively movable to effect separation of the first and second portions and thereby constitute the capsule opening means.

10. Apparatus as claimed in claim 9 wherein the second gripping means comprises a collet of variable diameter being connected to the body and defining an aperture through which a capsule is received at the dispensing station, the end cap being provided with third cam formations cooperable with the collet to reduce the aperture in response to movement of the end cap relative to the body to thereby grip the rear portion of a capsule.

11. Apparatus as claimed in claim 9 comprising latch means operable between the body and the end cap for retaining the end cap in a fixed position relative to the body during a first stage of movement of the actuator relative to the body and to release the end cap from the body so as to travel in unison with the actuator during a second stage of motion of the actuator relative to the body.

12. Apparatus as claimed in claim 11 wherein the latch means comprises at least one latch member connected to the end cap and cooperable with a corresponding recess formed in the body to prevent relative motion between the end cap and the body and wherein the actuator comprises at least one second cam formation cooperable with said at least one latch member to control the operation thereof according to the position of the actuator relative to the body.

13. Apparatus as claimed in claim 9 wherein the end cap defines a passageway receiving the forward portion of a capsule and the first gripping means comprises an O-ring located in the passageway.

14. Apparatus as claimed in claim 13 wherein the passageway communicates with an ejection aperture defined by the end cap and through which spent capsules are ejected in use.

15. A method of dispensing for inhalation medicaments supplied in capsules comprising the steps of locating a number of capsules in a capsule storage means defined by a body, operating a feed mechanism by movement of an actuator relative to the body to feed a capsule from the storage means to a dispensing station, operating a capsule opening means at the dispensing station by movement of the actuator relative to the body to expose the contents of the capsule within a dispensing chamber and inhaling a flow of air through an outlet communicating with the dispensing chamber via an airway such that the contents of the capsules are entrained in the flow of inhaled air, wherein the method comprises locating the capsules in linear array in a cylindrical portion of a storage chamber defined by the capsule storage means and wherein the feed mechanism is operable at each successive actuation to push a capsule longitudinally along the cylindrical portion towards the dispensing station by action of at least one feed member of the feed mechanism.

16. A method as claimed in claim 15 including the step of maintaining an end cap in fixed relationship to the body during a first stage of movement by operation of a latch means and moving the end cap in unison with the actuator during a second stage of motion, and actuating the capsule opening means by relative movement between the end cap and the body.

17. A method as claimed in claim 15 including the step of ejecting a portion of a spent capsule by action of the feed mechanism feeding a next successive capsule into the dispensing station to thereby displace the spent capsule portion.

18. Dispensing apparatus for use in the inhalation of medicaments supplied in capsules, the apparatus comprising a body having a capsule storage means receiving a number of capsules in use, an actuator movably mounted on the body, a dispensing station defining a dispensing chamber, a feed mechanism operable at successive actuations of the actuator to feed successive capsules from the storage chamber to the dispensing station, capsule opening means operable in response to movement of the actuator to expose at the dispensing station the contents of the capsule within the dispensing chamber and a duct defining an airway communicating between the dispensing chamber and an outlet defined by the body through which air is inhaled in use, the capsule storage means defining a storage chamber having a cylindrical portion to receive capsules arranged in linear array and the feed mechanism comprising first and second feed member means operable at successive actuations for moving a capsule longitudinally along the cylindrical portion towards the dispensing station, the apparatus further comprising a generally tubular end cap into which the body extends longitudinally, the end cap comprising a first gripping means operable to grip a forward portion of a capsule at the dispensing station, the body comprising second gripping means operable to grip a rear portion of a capsule at the dispensing station, the end cap being movable relative to the body in response to movement of the actuator whereby the first and second gripping means are relatively movable to effect separation of the front and rear portions and thereby constitute the capsule opening means.

19. Apparatus as claimed in claim 18 wherein the second gripping means comprises a collet of variable diameter being connected to the body and defining an aperture through which a capsule is received at the dispensing station, the end cap being provided with third cam formations cooperable with the collet to reduce the aperture in response to movement of the end cap relative to the body to thereby grip the rear portion of a capsule.

20. Apparatus as claimed in claim 18 wherein the end cap defines a passageway receiving the forward portion of a capsule and the first gripping means comprises an O-ring located in the passageway.

21. Apparatus as claimed in claim 20 wherein the passageway communicates with an ejection aperture defined by the end cap and through which spent capsules are ejected in use.

22. Apparatus as claimed in claim 18 further comprising latch means operable between the body and the end cap for retaining the end cap in a fixed position relative to the body during a first stage of movement of the actuator relative to the body and to release the end cap from the body so as to travel in unison with the actuator during a second stage of motion of the actuator relative to the body.

23. Apparatus as claimed in claim 22 wherein the latch means comprises at least one latch member connected to the end cap and cooperable with a respective recess formed in the body to prevent relative motion between the end cap and the body and wherein the actuator comprises second cam formations cooperable with respective latch members to control the operation thereof according to the position of the actuator relative to the body.

24. Dispensing apparatus for use in the inhalation of medicaments supplied in capsules, the apparatus comprising a body having a capsule storage means receiving a number of capsules in use, an actuator movably mounted on the body, a dispensing station defining a dispensing chamber, a feed mechanism operable at successive actuations of the actuator to feed successive capsules from the storage chamber to the dispensing station, capsule opening means operable in response to movement of the actuator to expose at the dispensing station the contents of the capsule within the dispensing chamber and a duct defining an airway communicating between the dispensing chamber and an outlet defined by the body through which air is inhaled in use, the capsule storage means defining a storage chamber having a cylindrical portion to receive capsules arranged in linear array and the feed mechanism comprising first and second feed member means operable at successive actuations for moving a capsule longitudinally along the cylindrical portion towards the dispensing station, and wherein the actuator comprises a tubular sleeve overlaying the body reciprocatingly movable relative to the body in a direction coaxial with the cylindrical portion.

25. Apparatus as claimed in claim 24 wherein the first and second feed member means are operatively connected to the actuator by respective jaws facilitating movement of the feed member means into and out of operative engagement with capsules within the cylindrical portion of the storage chamber, the jaws being formed separately from the actuator and wherein the feed mechanism further comprises biassing means operable between the body and the jaws to bias the jaws longitudinally towards the dispensing station, the actuator being engageable with the jaws to move the jaws away from the dispensing station and operable to release the jaws for travel towards the dispensing station by action of the biassing means.

26. Dispensing apparatus for use in the inhalation of medicaments supplied in capsules, the apparatus comprising a body having a capsule storage means receiving a number of capsules in use, an actuator movably mounted on the body, a dispensing station defining a dispensing chamber, a feed mechanism operable at successive actuations of the actuator to feed successive capsules from the storage chamber to the dispensing station, capsule opening means operable in response to movement of the actuator to expose at the dispensing station the contents of the capsule within the dispensing chamber and a duct defining an airway communicating between the dispensing chamber and an outlet defined by the body through which air is inhaled in use, the capsule storage means defining a storage chamber having a cylindrical portion to receive capsules arranged in linear array and the feed mechanism comprising first and second feed member means operable at successive actuations for moving a capsule longitudinally along the cylindrical portion towards the dispensing station, said feed member means being operatively connected to the actuator by respective jaws facilitating movement of the feed member means into and out of operative engagement with capsules within the cylindrical portion of the storage chamber, and wherein the body is provided with first cam formations cooperable with the feed member means such that the jaws are moved to a closed position during at least part of a forward longitudinal motion of the jaws towards the dispensing station and are retraced to an open position during return motion of the jaws relative to the body, the closed portion of the jaws corresponding to the respective feed member means being operatively engageable with a capsule within the cylindrical portion and the open position corresponding to the feed member means being retracted out of operative engagement with the capsules.

27. Dispensing apparatus for use in the inhalation of medicaments supplied in capsules, the apparatus comprising a body having a capsule storage means receiving a number of capsules in use, an actuator movably mounted on the body, a dispensing station defining a dispensing chamber, a feed mechanism operable at successive actuations of the actuator to feed successive capsules from the storage chamber to the dispensing station, capsule opening means operable in response to movement of the actuator to expose at the dispensing station the contents of the capsule within the dispensing chamber and a duct defining an airway communicating between the dispensing chamber and an outlet defined by the body through which air is inhaled in use, the capsule storage means defining a storage chamber having a cylindrical portion to receive capsules arranged in linear array and the feed mechanism comprising first and second feed members operable at successive actuations to move a capsule longitudinally along the cylindrical portion towards the dispensing station, wherein the body comprises a mouthpiece defining the outlet, the mouthpiece being connected to a tube defining the storage chamber, the mouthpiece and the tube being removably connected to a main portion of the body to provide access to the storage chamber.

* * * * *